United States Patent [19]
Francotte

[11] Patent Number: 6,011,149
[45] Date of Patent: Jan. 4, 2000

[54] PHOTOCHEMICALLY CROSS-LINKED POLYSACCHARIDE DERIVATIVES AS SUPPORTS FOR THE CHROMATOGRAPHIC SEPARATION OF ENANTIOMERS

[75] Inventor: Eric Francotte, Nuglar, Switzerland

[73] Assignee: Novartis AG, Basel, Switzerland

[21] Appl. No.: 08/894,976

[22] PCT Filed: Feb. 24, 1996

[86] PCT No.: PCT/EP96/00773

§ 371 Date: Sep. 2, 1997

§ 102(e) Date: Sep. 2, 1997

[87] PCT Pub. No.: WO96/27615

PCT Pub. Date: Sep. 12, 1996

[30] Foreign Application Priority Data

Mar. 7, 1995 [CH] Switzerland ................. 640/95

[51] Int. Cl.$^7$ .............. C07H 1/00; C07H 3/00; C08B 3/00; C08B 15/10
[52] U.S. Cl. ............ 536/58; 536/124; 536/123.1; 536/110; 536/56
[58] Field of Search ................ 536/123.1, 124, 536/56, 58, 110

[56] References Cited

U.S. PATENT DOCUMENTS

| | | |
|---|---|---|
| 3,960,685 | 6/1976 | Sano et al. . |
| 4,107,174 | 8/1978 | Baumann et al. ................ 260/326 |
| 4,861,872 | 8/1989 | Okamoto et al. ................ 536/18.7 |

FOREIGN PATENT DOCUMENTS

| | | |
|---|---|---|
| 0321882 | 6/1989 | European Pat. Off. . |
| 0 554 898 A2 | 8/1993 | European Pat. Off. . |
| 9213894 | 8/1992 | WIPO . |

OTHER PUBLICATIONS

L. Oliveros, et al., Journal of Liquid Chromatography, vol. 18, No. 8, 1995, pp. 1521–1532.

*Primary Examiner*—Gary L. Kunz
*Attorney, Agent, or Firm*—Gabriel Lopez; Stephen G. Kalinchak

[57] ABSTRACT

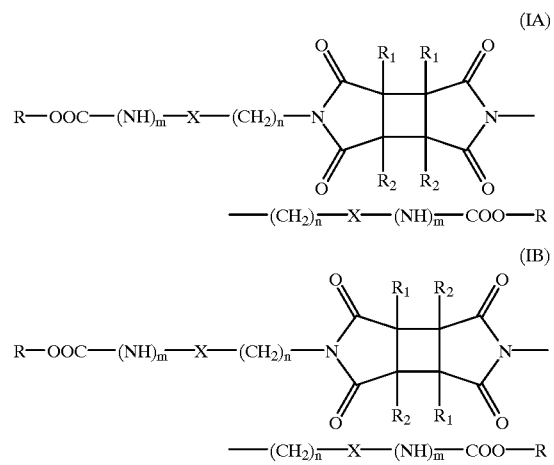

The present invention relates to photochemically cross-linked derivatives of general formulae (IA) and (IB), wherein R is a polysaccharide radical in which the OH groups have been esterified as OR' groups or converted into a carbamate (urethane), $R_1$, and $R_2$ are each independently lower alkyl or unsubstituted or substituted aryl, X is a direct bond or phenylene, m is 0 or 1, and n is 0 or an integer from 1 to 20, to processes from the preparation thereof and to the use thereof. The compounds of general formula (IA) and (IB) can be used as supports in the chromatographic separation of enantiomers.

21 Claims, No Drawings

PHOTOCHEMICALLY CROSS-LINKED POLYSACCHARIDE DERIVATIVES AS SUPPORTS FOR THE CHROMATOGRAPHIC SEPARATION OF ENANTIOMERS

This is a 371 of International Application PCT/EP 96/00773, filed Feb. 24, 1996.

The invention relates to substantially photochemically cross-linked polysaccharide derivatives that are used as supports in the chromatographic separation of enantiomers.

DE-A-2 422 365 describes polymers that are suitable for photopolymerisation, having anhydride-containing groups, that are converted by means of mechanically active light into resistant substances that are suitable as protective printing compositions or also for the manufacture of protective printing screens for printing plates.

N. R. Bertoniere et al. describe in J. Appl. Polymer Sci., Vol. 15, (1971) 1743 woven cotton fabrics having as substituents cinnamic acid esters (cinnamoyl radicals) which when irradiated with light of a specific wavelength (2573 Å) first isomerise and then dimerise to truxillic and truxinic acid derivatives, the photochemical reaction taking place mainly on the surface of the fabric.

The two U.S. Pat. Nos. 2,682,481 and 2,682,482 describe methods by which soluble carbohydrates, especially cellulose derivatives, that carry unsaturated functional groups are converted by heating with peroxide catalysts and dimerisation or further cross-linking into shaped articles having an insoluble surface.

E. Yashima et al. describe in J. Chromatography A, 677(1994), 11–19 3,5-dimethylphenylcarbamates of cellulose and amylose that are bonded at specifically selected sites to silica gel and are used as a chiral stationary phase for HPL chromatography (high-pressure liquid chromatography). The 3,5-dimethylphenylcarbamates of cellulose and amylose are bonded to the 3-aminopropyl silica gel via 4,4'-diphenylmethane isocyanate as intermediate members. Since those chemically bonded phases are not damaged by polar solvents, such as $CHCl_3$ (chloroform), a small amount of $CHCl_3$ can be added to the eluant for effective separation of racemates and of enantiomers.

Y. Okamoto et al. describe in J. Liquid Chromatography 10, 1613–1698 (1987), cellulose-tris(3,5-dimethylphenylcarbamates) and -tris(3,5-dichlorophenylcarbamates) that are chemically bonded to 3-aminopropyl silica gel via 4,4'-diphenylmethane isocyanate.

As the first process step for the preparation, first the cellulose is bonded via the diisocyanate to the 3-aminopropyl silica gel. The reaction product is then treated with a large excess of 3,5-dimethylphenyl isocyanate or 3,5-dichlorophenyl isocyanate to produce the corresponding carbamates of cellulose.

The optical separating power of the chiral stationary phase is compared to that obtained by coating silica gel with cellulose triphenyl carbamates, it being possible to vary the chiral separating capacity of the stationary phase by heat treatment.

In a poster exhibited at the 5th Intern. Symposium "On Chiral Discrimination" in Stockholm in October, 1994, L. Oliveros et al. describe stationary phases consisting of 3,5-dimethylphenylcarbamate cellulose that have been immobilised on a support. It is not clear from the data given on the poster whether the chiral material has been immobilised and has any particular advantages over known materials from the prior art.

The present invention relates to photochemically cross-linked polysaccharide derivatives of the general formulae IA and IB

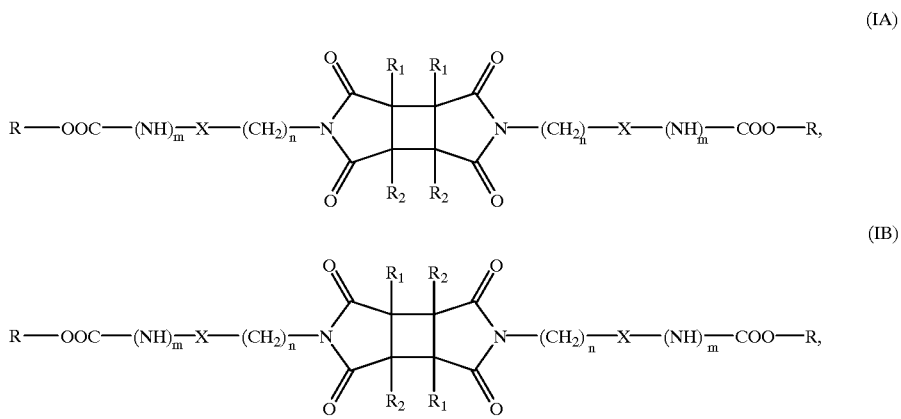

wherein
R is a polysaccharide radical in which the OH groups have been esterified as OR' groups or converted into a carbamate (urethane),
$R_1$ and $R_2$ are each independently lower alkyl or unsubstituted or substituted aryl,
X is a direct bond or phenylene,
m is 0 or 1 and
n is 0 or an integer from 1 to 20.

The invention relates especially to photochemically cross-linked polysaccharide derivatives of the general formulae IA and IB, wherein
R is a cellulose or amylose radical in which the OH groups have been esterified as OR' groups or converted into a carbamate (urethane),
$R_1$ and $R_2$ are each independently methyl or ethyl or an unsubstituted or substituted phenyl and
X is a direct bond or phenylene,
m is 0 or 1, and
n is 0 or an integer from 1 to 12.

Of very special importance are photochemically cross-linked polysaccharide derivatives of the general formulae IA and IB, wherein
R is a cellulose radical in which the OH groups have been esterified as OR' groups or converted into a carbamate (urethane), $R_1$ and $R_2$ are methyl and X is a direct bond or phenylene, m is 0 or 1 and n is 0 or an integer from 1 to 12.

The invention relates to the compounds of formulae 1A and 1B characterised in the Examples.

Hereinbefore and hereinafter, lower radicals and compounds are to be understood, for example, as those having up to and including 7, preferably up to and including 4, carbon atoms (C atoms).

Polysaccharides are, for example, cellulose, amylose, chitosan, dextran, xylan and inulin, which are obtainable as polysaccharides in a high degree of purity. Preference is given to polysaccharides having a degree of polymerisation (number of pyranose and furanose rings) of at least 5, and especially at least 10, but 1000 should not be exceeded in order to ensure ease of handling.

Lower alkyl is, for example, $C_1$–$C_4$alkyl, such as methyl, ethyl, propyl or butyl, which may also be substituted by halogen, such as fluorine or chlorine, such as trifluoromethyl or trichloromethyl.

Aryl as such is, for example, phenyl or naphthyl, such as 1- or 2-naphthyl, or substituted phenyl or naphthyl, such as phenyl or naphthyl substituted by lower alkyl, halo-lower alkyl, hydroxy, lower alkoxy, lower alkanoyloxy, halogen, cyano and/or by nitro.

Aryl is preferably phenyl that is unsubstituted or substituted as indicated above, and is especially phenyl.

Lower alkoxy is, for example, n-propoxy, isopropoxy, n-butoxy or tert-butoxy, preferably ethoxy and especially methoxy.

Lower alkanoyloxy is, for example, propionyloxy or pivaloyloxy, preferably acetyloxy.

Halogen is, for example, chlorine or fluorine, also bromine or iodine.

Halo-lower alkyl is, for example, 2- or 3-halo-lower alkyl, such as 2-halo-lower alkyl, such as 2-halopropyl, 3-halopropyl or 3-halo-2-methyl-propyl.

The compounds of the general formulae IA and IB are prepared by cross-linking compounds of the general formula II

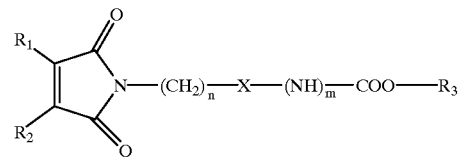

wherein

R is a polysaccharide radical in which the OH groups have been esterified as OR' groups or converted into a carbamate (urethane), and $R_1$ and $R_2$, n and m are as defined for formulae IA and IB, after previously applying them as a coating to a support or, after previously conditioning them, in the form of the pure material using an emulsion, by (hv) irradiation to form compounds of the general formulae IA and IB.

The cross-linking is effected by irradition using a submersible mercury lamp. Suitable suspension agents are, for example, inert solvents, for example hydrocarbons, such as hexane or lower alkanols, such as methanol, ethanol, propanol or isopropanol or aqueous mixtures thereof, or ethereal solvents, such as, for example, diethyl ether.

There may be used as support silicon dioxides, such as silica gel, especially aminosilanised silica gel, also aluminium oxide (alumina), graphite and zirconium oxide (zirconia).

Polysaccharide compounds of the general formula II wherein

R is a polysaccharide radical in which the OH groups have been esterified as OR' groups or converted into a carbamate (urethane), and $R_1$ and $R_2$, X, m and n are as defined for formulae IA and IB are novel and form part of the invention and can be prepared by methods known per se.

Of special importance are compounds of the general formula II wherein

R is a cellulose or amylose radical in which the OH groups have been esterified as OR' groups or converted into a carbamate, and $R_1$ and $R_2$ are each independently methyl or unsubstituted or substituted phenyl and X, m and n are as defined for formulae IA and IB.

Of very special importance are compounds of the general formula II wherein

R is a cellulose radical in which the OH groups have been esterified as OR' groups or converted into a carbamate, and $R_1$ and $R_2$ are methyl and X, m and n are as defined for formulae IA and IB.

Compounds of the general formula II are prepared as follows: in compounds of the general formula III

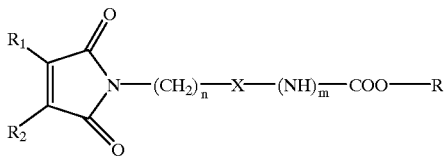

wherein $R_3$ is a polysaccharide radical having free OH groups, and $R_1$ and $R_2$, X, m and n are as defined for formulae IA and IB, the free OH groups are esterified as OR' groups or converted into a carbamate (urethane).

The esterification and the preparation of the carbamate are effected in a manner known per se by reaction with an isocyanate or a reactive functional carboxylic acid derivative.

For example, the esterification can be effected with unsubstituted or substituted benzoyl halides, especially benzoyl chlorides, the corresponding carboxylic acid anhydrides or also with a mixture of the corresponding carboxylic acid and a suitable dehydrating agent.

There can be used for the esterification any inert solvent that does not impede the esterification. Preference is given to the use of pyridine or also quinoline, a catalyst, for example a tertiary amine, such as 4-(N,N-dimethylarnino) pyridine, generally also being added.

The preparation of the carbamate is customarily effected by reaction with a suitable isocyanate in the presence of a suitable catalyst. There may be used as catalyst Lewis bases, such as tertiary amines, or also Lewis acids, such as a tin compound. The reaction is preferably carried out in the presence of a tertiary base, such as in the presence of pyridine or quinoline, which at the same time serve also as solvents, although there is also preferably used as tertiary base 4-(N,N-dimethylamino)pyridine, as a reaction accelerator.

For the conversion of the OH groups into the corresponding OR' groups by esterification or the preparation of the carbamate there are used, especially, unsubstituted or substituted benzoyl chlorides or phenyl isocyanates. Preference is given to the use of chloro- or methyl-substituted, especially mono- or di-substituted chloro- and/or methyl-substituted, phenyl isocyanates or benzoyl chlorides, and the methyl groups can be in meta- or ortho-position relative to one another.

Compounds of the general formula III are novel and the invention relates also thereto.

Of special importance are polysaccharide compounds of the general formula III wherein
R$_3$ is a cellulose or amylose radical having free OH groups and R$_1$ and R$_2$ are each independently methyl or unsubstituted or substituted phenyl, and X, m and n are as defined for formulae IA and IB.

Of very special importance are polysaccharide compounds of the general formula III wherein R$_3$ is a cellulose or amylose radical having free OH groups and R$_1$ and R$_2$ are methyl, and X, m and n are as defined for formulae IA and IB.

Compounds of the general formula III are obtained by converting into a carbamate or esterifying polysaccharides having free OH groups with an imidylcarboxylic acid halide or isocyanate of formula IV

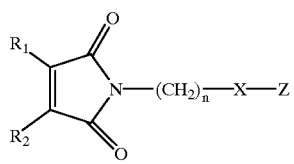

IV wherein R$_1$, R$_2$, n and X are as defined for formulae IA and IB and Z is an isocyanate group (–N=C=O) or a carboxylic acid halide group, especially a carboxylic acid chloride group, where appropriate in the presence of a catalyst. The reactions are carried out as described hereinbefore.

For example, the reaction with an acid chloride is carried out in the presence of a basic condensation agent, for example with a tertiary organic base, such as a tri-lower alkylamine, such as triethylamine, or an organic nitrogen base, such as pyridine or quinoline, especially dimethylaminopyridine, in a temperature range of from 10 to 130° C., preferably in a temperature range of from 20 to 90° C.

The reaction with an imidyl isocyanate of formula IV is carried out where appropriate also in the presence of a catalyst, for example in the presence of dibutyltin dilaurate in a suspension agent, for example pyridine.

Some compounds of the general formula IV wherein Z is a carboxylic acid chloride group (—COCl) are known and can be prepared by the process mentioned in CH-A-599 153. Others can be prepared in analogous manner.

From the correspondingly obtained (2,5-dihydro-3,4-(disubst.)-2,5-dioxo-pyrrol-1-yl)-carboxylic acid chlorides of formula IV there can be obtained by reaction with aqueous sodium azide solution in toluene in the presence of benzyltriethylammonium chloride the corresponding isocyanates of the general formula IV.

The photochemically cross-linked polysaccharides of the general formulae IA and IB according to the invention are, surprisingly, suitable as supports when methylene chloride (CH$_2$Cl$_2$), tetrahydrofuran and chloroform form a proportion of the mobile phase and are, surprisingly, far superior to the supports known hitherto from the prior art.

Separation of enantiomers with a mobile phase comprising methylene choride, or tetrahydrofuran or dioxane, can, surprisingly, be carried out advantageously.

In the case of certain racemates especially, better separation results have been achieved when using specific amounts of methylene chloride as mobile phase than with supports from the prior art. That surprising improvement in the separation results was attributable to the use of methylene chloride.

The photochemically cross-linked polysaccharides of the general formulae IA and IB in conditioned form can also be used as pure polymers for the chromatographic separation of enantiomers.

The various chromatographic separations of enantiomers are described and explained in more detail at the end of the preparation section (Examples).

The following Examples (including the preparation of the starting materials and intermediates) serve to illustrate and to provide further clarification of the invention.

Temperatures are given in degrees Celsius and pressures, unless otherwise indicated, in bars.

INTERMEDIATE 1

Preparation of (2,5-dihydro-3,4-dimethyl-2,5-dioxo-pyrrol-1-yl)-acetyl chloride)

183.2 g (1 mol) of (2,5-dihydro-3,4-dimethyl-2,5-dioxo-pyrrol-1-yl)acetic acid are suspended in 360 ml of toluene. The solution is heated under reflux for 16 hours using a water separator. During that period, approx. 40 ml of toluene/water are distilled off azeotropically. The solution is then cooled to 70° C. and 76.3 ml of thionyl chloride are added dropwise in the course of 90 minutes. As soon as the evolution of gas has ceased (approx. 2 hours), the temperature is increased to 90° C. for 2 hours and then to 110° C. for 30 minutes. After cooling, the solution is concentrated. The liquid residue is distilled and the fraction that boils at 182–184° C. is collected. Yield: 172.5 g (85.5%). Elemental analysis: Calc.: C 46.66; H 4.00; N 5.95; O 23.81; Cl 17.58. Found: C 49.42; H 4.21; N 6.71; O 22.93; Cl 16.83. $^1$H-NMR (CDCl$_3$: 2 (s, CH$_3$), 4.63 (s, CH$_2$).

INTERMEDIATE 2

Preparation of (2,5-dihydro-3,4-dimethyl-2,5-dioxo-pyrrol-1-yl)-methyl isocyanate With vigorous stirring, a mixture of aqueous sodium azide (26.3 g in 80 ml of water), 160 ml of toluene and 1.5 ml of benzyltriethylarnmonium chloride is cooled at approx. 10° C. in a 750 ml sulfonating flask. 80.64 g of acid chloride 1 are added dropwise to that solution in the course of approx. 40 minutes. Stirring of the solution is then continued for 1 hour at 15° C. and then for 1 hour at 20° C. The organic phase is separated off in a separating funnel and washed in succession with 2N aqueous sodium hydrogen carbonate solution and with water. The organic phase is dried with sodium sulfate and filtered. The filtrate is introduced into a 750 ml sulfonating flask and heated slowly to the reflux temperature. Reflux is maintained until the evolution of nitrogen has ceased. The solution is then heated under reflux for a further 30 minutes and, after cooling, is poured into a round-bottomed flask. The solution is concentrated using a rotary evaporator and the residue is distilled under a high vacuum (0.045 mm Hg). Boiling point: 90° C. Yield: 64.3 g (89.2%). Elemental analysis: Calc.: C 53.33; H 4.48; N 15.55; O 26.64. Found: C 53.17; H 4.51; N 15.61; O 26.80. $^1$H-NMR (CDCl$_3$): 2 (s, CH$_3$), 4.95 (s, CH$_2$).

INTERMEDIATE 3

Preparation of 2-(2,5-dihydro-3,4-dimethyl-2,5-dioxo-pyrrol-1-yl)-butanoic acid chloride 30.1 g of 2-(2,5-dihydro-3,4-dimethyl-2,5-dioxo-pyrrol-1-yl) butanoic acid are suspended in 50 ml of toluene. The solution is heated under reflux for 16 hours using a water separator. During that period, approx. 50 ml of toluene/water are distilled off azeotropically. The solution is then cooled to 70° C. and 12.4 ml of thionyl chloride are added dropwise thereto in the course of 90 minutes. As soon as the evolution of gas has ceased (approx. 2 hours), the temperature is increased to 90° C. for 2 hours and then to 110° C. for 30 minutes. After cooling, the solution is concentrated using a rotary evaporator. The solid residue is isolated and dried under a high vacuum. Melting point: 68° C. Yield: 32.5 g (99.3%). Elemental analysis: Calc.: C 52.30; H 5.27; N 6.10; O 20.90; Cl 15.44. Found: C 53.60; H 5.30; N 6.15; O 21.33; Cl 14.40. $^1$H-NMR (CDCl$_3$): 1.93 (quint, CH$_2$), 1.95 (s, CH$_3$), 2.37 (t, CH$_2$), 3.55 (t, CH$_2$).

INTERMEDIATE 4

Preparation of 4-(2,5-dihydro-3,4-dimethyl-2,5-dioxo-pyrrol-1-yl)-1-propyl isocyanate Analogously to the preparation of Intermediate 2, 37.8 g of acid chloride 3 are reacted with 10.9 g of sodium azide (in 40 ml of water) in the presence of 0.7 g of benzyltriethylammonium chloride in 80 ml of toluene. After rearrangement of the acyl azide, the solution is concentrated and the residue is distilled under a high vacuum (0.075 mm Hg). The fraction that boils at 88–100° C. is collected. Yield: 5.8 g (17%). Elemental analysis: Calc.: C 57.69; H 5.81; N 13.45; O 23.05. Found: C 57.47; H 5.86; N 13.23; O 23.21. $^1$H-NMR (CDCl$_3$): 1.84 (quint, CH$_2$),1.94 (s, CH$_3$), 3.30 (t, CH$_2$), 3.55 (t, CH$_2$). IR (CDCl$_3$): 2240 cm$^{-1}$, isocyanate; 1890 cm$^{-1}$, amide.

INTERMEDIATE 5

Preparation of 2-(2,5-dihydro-3,4-dimethyl-2,5-dioxo-pyrrol-1-yl)-hexanoic acid chloride 71.5 g of 2-(2,5-dihydro-3,4-dimethyl-2,5-dioxo-pyrrol-1-yl)-hexanoic acid are suspended in 150 ml of toluene and the solution is heated under reflux for 16 hours using a water separator. During that period, approx. 5 ml of toluene/water are distilled off azeotropically. The solution is then cooled to 70° C. and 22.5 ml of thionyl chloride are added dropwise in the course of 90 minutes. As soon as the evolution of gas has ceased (approx. 2 hours), the temperature is increased to 90° C. for 2 hours and then to 110° C. for 30 minutes. After cooling, the solution is concentrated using a rotary evaporator. The solid residue is isolated and dried under a high vacuum. Yield: 70.9 g (92%). Melting point: 43° C. Yield: 32.5 g (99.3%). $^1$H-NMR (CDCl$_3$): 1.2–1.4 (m, CH$_2$), 1.45–1.75 (m, CH$_2$), 1.92 (s, CH$_3$), 2.85 (t, CH$_2$), 3.45 (t, CH$_2$).

INTERMEDIATE 6

Preparation of 5-(2,5-dihydro-3,4-dimethyl-2,5-dioxo-pyrrol-1-yl)-1-pentyl isocyanate Analogously to the preparation of Intermediate 2, 51.5 g of acid chloride 5 are reacted with 13.1 g of sodium azide (in 30 ml of water) in the presence of 0.4 g of benzyltriethylammonium chloride in 200 ml of toluene. After rearrangement of the acyl azide the solution is concentrated using a rotary evaporator and the residue is distilled under a high vacuum (0.045 mm Hg). The fraction that boils at 123–125° C. is collected. Yield: 36.6 g (79%). Elemental analysis: Calc.: C 61.00; H 6.83; N 11.86; O 20.31. Found: C 61.00; H 6.88; N 11.80; O 20.41. $^1$H-NMR (CDCl$_3$): 1.2–1.35 (m, CH$_2$), 1.45–1.60 (m, CH$_2$), 1.88 (s, CH$_3$), 3.23 (t, CH$_2$), 3.41 (t, CH$_2$). IR (CH$_2$Cl$_2$): 2250 cm$^{-1}$, isocyanate; 1885 cm$^{-1}$, amide.

INTERMEDIATE 7

Preparation of 4-(2,5-dihydro-3,4-dimethyl-2,5-dioxo-pyrrol-1-yl)-benzoic acid chloride 48 g (0.35 mol) of 4-aminobenzoic acid are dissolved in sodium hydroxide solution (14 g of NaOH in 300 ml of water). To that mixture there is added dropwise, with stirring, a solution of 44.2 g of dimethylmaleic acid anhydride in 300 ml of dimethylacetamide. The solution is then heated at 90° C. and, after 1.30 hours, 175 ml of aqueous hydrochloric acid (2N) are added. After the addition of hydrochloric acid, the solution is cooled to room temperature and the stirrer is switched off. The crystalline product that has precipitated is filtered off, washed with water and dried in vacuo at 60° C. Yield: 73.6 g (85.7%). Melting point: 230–231° C. 73.6 g of that intermediate are suspended in 700 ml of dry toluene. At 70° C., 32 ml of thionyl chloride are added dropwise. As soon as the evolution of gas has ceased (approx. 2 hours), the temperature is increased to 80° C. for 2 hours. After cooling, the solution is concentrated using a rotary evaporator. The solid residue is recrystallised from toluene and then dried at 60° C. Yield: 88%. Melting point: 199–200° C. $^1$H-NMR (CDCl$_3$): 2.08 (s, CH$_3$), 7.68 (d, phenyl), 8.20 (d, phenyl).

INTERMEDIATE 8

Preparation of 4-(2,5-dihydro-3,4-dimethyl-2,5-dioxo-pyrrol-1-yl)-phenyl isocyanate With vigorous stirring, a mixture of aqueous sodium azide (4.6 g in 14 ml of water), 28 ml of toluene and 0.5 g of benzyltriethylammonium chloride is cooled to approx. 0° C. in a 250 ml sulfonating flask. To that solution there are added in the course of approx. 40 minutes 18.5 g of acid chloride 7. Stirring of the solution is then continued for 1 hour at 50° C. and then for 20 hours at room temperature. 150 ml of ethyl acetate are added to the solution and the mixture is then diluted in a separating funnel with 600 ml of ethyl acetate and 200 ml of water. The organic phase is separated off, washed three times with 200 ml of water each time, dried over sodium sulfate and filtered. The filtrate is poured into a 2 liter round-bottomed flask and concentrated at 35° C. to approx. 600 ml using a rotary evaporator. The solution is heated slowly to approx. 60–70° C. and that temperature is maintained until the evolution of nitrogen has ceased (approx. 1 hour). Ethyl acetate is distilled off and the residue is then dried at 130° C. for 1 hour under a water-jet vacuum. The light yellow solid residue is used without further purification. Yield: 16.8 g (98%). Elemental analysis: Calc. C 64.46; H 4.16; N 11.56; O 19.81. Found: C 64.45; H 4.23; N 11.75; O 19.66. $^1$H-NMR (CDCl$_3$): 2.07 (s, CH$_3$), 7.2–7.4 (m, phenyl).

INTERMEDIATE 9

Preparation of 4-[(2,5-dihydro-3,4-dimethyl-2,5-dioxo-pyrrol-1-yl)methyl]-benzoic acid chloride 100 g (0.66 mol) of 4-(aminomethyl)-benzoic acid are dissolved in sodium hydroxide solution (26.4 g of NaOH in 300 ml of water). There is added dropwise to that solution, with stirring, a solution of 83.3 g of dimethylmaleic acid anhydride in 500 ml of dimethylacetamide. The reaction solution is then heated at 90° C. and, after 1.5 hours, 330 ml of aqueous hydrochloric acid (2N) are added. After the addition of hydrochloric acid the solution is cooled to room temperature and the stirrer is switched off. The crystalline product that has precipitated is filtered off, washed with water and dried in vacuo at 60° C. Yield: 155 g (90%). Melting point: 182–183° C. 120 g of that intermediate are suspended in 1000 ml of dry toluene. At 70° C., 50 ml of thionyl chloride are added dropwise. As soon as the evolution of gas has ceased (approx. 2 hours), the temperature is increased to 80° C. for 2 hours. After cooling, the solution is concentrated. The solid residue is recrystallised in toluene and then dried at 60° C. Yield: 155 g (80%). Melting point: 98–99° C. $^1$H-NMR (CDCl$_3$): 1.98 (s, CH$_3$), 4.72 (s, CH$_2$), 7.45 (d, phenyl), 8.06 (d, phenyl).

INTERMEDIATE 10

Reaction of cellulose with (2,5-dihydro-3,4-dimethyl-2,5-dioxo-pyrrol-1-yl)-acetyl chloride 10.4 g of cellulose (Serva HL, from cotton linters) are dried for 4.5 hours in a flask at a bath temperature of 125° C. with nitrogen flushing (9.6 g after drying). Then 70 ml of pyridine, 21 ml of triethylamine, 0.2 g of dimethylaminopyridine and 1.81 g of Intermediate 1 are added at room temperature. The suspension is stirred at 90° C. for 24 hours. After cooling, 850 ml of methanol are added to the suspension which is then filtered and washed with methanol. The residue is again suspended in 200 ml of methanol, stirred for 1 hour at room temperature, filtered and washed with methanol. Yield: 10.3 g. Elemental analysis: Found: C 42.51; H 6.49; N <0.30; O 51.10.

INTERMEDIATE 11

Reaction of the decomposed cellulose with (2,5-dihydro-3,4-dimethyl-2,5-dioxo-pyrrol-1-yl)-acetyl chloride 10.2 g of decomposed cellulose (degree of polymerisation approx. 30) are dried for 6 hours in a flask at a bath temperature of 125° C. with nitrogen flushing (9.7 g after drying). Then 60 ml of pyridine, 21 ml of triethylamine, 0.2 g of dimethylaminopyridine and 1.81 g of Intermediate 1 are added at room temperature. The suspension is stirred at 90° C. for 24 hours. After cooling, 1000 ml of methanol are added to the suspension which is then filtered and washed with methanol. The residue is again suspended in 200 ml of methanol, stirred for 1 hour at room temperature, filtered and washed with methanol. Yield: 10.3 g. Elemental analysis: Found: C 40.91; H 6.66; N 0.49; O 52.10.

INTERMEDIATE 12

Reaction of cellulose with 4-(2,5-dihydro-3,4-dimethyl-2,5-dioxo-pyrrol-1-yl)-benzoic acid chloride.

Analogously to the preparation of Intermediate 10, 10.4 g of cellulose are reacted with 2.4 g of benzoyl chloride derivative 7. Yield after working-up: 10.4 g. Elemental analysis: Found: C 43.03; H 6.48; N 0.34; O 50.01.

INTERMEDIATE 13

Reaction of the decomposed cellulose with 4-(2,5-dihydro-3,4-dimethyl-2,5-dioxo-pyrrol-1-yl)-benzoic acid chloride 1 g of decomposed cellulose (degree of polymerisation approx. 30) are suspended in 90 ml of pyridine. To that mixture are added 1.6 g of (2,5-dihydro-3,4-dimethyl-2,5-dioxo-pyrrol-1-yl)-benzoic acid chloride 7 and 10 mg of dimethylaminopyridine as catalyst. Then 30 ml of triethylamine are added dropwise with continuous stirring. The solution is then stirred at 90° C. for 20 hours. After cooling, the resulting suspension is poured into 300 ml of ethanol and filtered. The white product is twice suspended in methylene chloride, filtered, washed and dried in vacuo. Yield: 1 g. Nitrogen content: N 1.27. The nitrogen content is consistent with a degree of substitution of 0.19 per glucose unit.

INTERMEDIATE 14

Reaction of cellulose with 4-[(2,5-dihydro-3,4-dimethyl-2,5-dioxo-pyrrol-1 -yl)-methyl]-benzoic acid chloride Analogously to the preparation of Intermediate 10, 10.4 g of cellulose are reacted with 2.5 g of benzoyl chloride derivative 9. Yield after working-up: 12 g. Elemental analysis: Found: C 45.56; H 6.39; N 0.73; O 48.02.

INTERMEDIATE 15

Reaction of the decomposed cellulose with 4-[(2,5-dihydro-3,4-dimethyl-2,5-dioxo-pyrrol-1 -yl) methyl]-benzoic acid chloride 3 g of decomposed cellulose (degree of polymerisation approx. 30) are suspended in 120 ml of pyridine. To that mixture are added 7.7 g of 4-[(2,5-dihydro-3,4-dimethyl-2,5-dioxo-pyrrol-1-yl)methyl]-benzoic acid chloride 9 and 10 mg of dimethylaminopyridine as catalyst. Then 15 ml of triethylamine are added dropwise with continuous stirring. The solution is stirred at 80° C. for 24 hours. After cooling, the resulting suspension is poured into 300 ml of methanol and filtered. The white product is twice suspended in methylene chloride, filtered, washed and dried in vacuo. Yield: 2.7 g. Elemental analysis: C 51.07; H 5.89; N 2.03; O 40.88. The nitrogen content is consistent with a degree of substitution of 0.36 per glucose unit.

INTERMEDIATE 16

Reaction of cellulose with (2,5-dihydro-3,4-dimethyl-2,5-dioxo-pyrrol-1-yl)-methyl isocyanate 10.4 g of cellulose (Serva HL, from cotton linters) are dried for 4.5 hours in a flask at a bath temperature of 125° C. with nitrogen flushing (9.6 g after drying). Then 60 ml of pyridine, 1.62 g of isocyanate derivative 2 and 0.2 ml of dibutyltin dilaurate are added. The suspension is stirred at 125° C. for 21 hours. After cooling, 200 ml of methanol are added to the suspension which is then stirred for 1 hour at room temperature and filtered. The solid residue is washed with methanol and dried under a high vacuum. Yield: 10.7 g. Elemental analysis: Found: C 43.07; H 6.21; N 1.06; O 49.88.

INTERMEDIATE 17

Reaction of the decomposed cellulose with (2,5-dihydro-3,4-dimethyl-2,5-dioxo-pyrrol-1-yl)-methyl isocyanate 5.1 g of decomposed cellulose (degree of polymerisation approx. 30) are dried for 4.5 hours in a flask at a bath temperature of 125° C. with nitrogen flushing (4.7 g after drying). Then 30 ml of pyridine, 0.72 g of isocyanate derivative 2 and 0.1 ml of dibutyltin dilaurate are added. The suspension is stirred for 21 hours at 125° C. After cooling, 200 ml of methanol are added to the suspension which is then stirred for 1 hour at room temperature and then filtered. The solid residue is washed with methanol and dried under a high vacuum. Yield: 5.2 g. Elemental analysis: Found: C 42.09; H 6.38; N 0.90; O 50.64.

INTERMEDIATE 18

Reaction of cellulose with 4-(2,5-dihydro-3,4-dimethyl-2,5-dioxo-pyrrol-1-yl)-1-propyl isocyanate Analogously to the preparation of Intermediate 17, 10.4 g of cellulose are reacted with 1.9 g of isocyanate derivative 4. Yield after working-up: 11.1 g. Elemental analysis: Found: C 42.96; H 6.44; N 1.14; O 49.16.

INTERMEDIATE 19

Reaction of cellulose with 5-(2,5-dihydro-3,4-dimethyl-2,5-dioxo-pyrrol-1-yl)-1-pentyl isocyanate Analogously to the preparation of Intermediate 17, 10.4 g of cellulose are reacted with 2.13 g of isocyanate derivative 6. Yield after working-up: 11.5 g. Elemental analysis: Found: C 44.30; H 6.44; N 1.59; O 47.24.

INTERMEDIATE 20

Reaction of cellulose with 4-(2,5-dihydro-3,4-dimethyl-2,5-dioxo-pyrrol-1-yl)-phenyl isocyanate Analogously to the preparation of Intermediate 17, 10.4 g of cellulose are reacted with 2.3 g of isocyanate derivative 8. Yield after working-up: 11.5 g. Elemental analysis: Found: C 44.81; H 6.03; N 1.30; O 48.06.

EXAMPLE 1

2.57 g of Intermediate 10 are dried in a round-bottomed flask for 3 hours at a bath temperature of 120° C. with nitrogen flushing. Then 40 ml of pyridine, 0.1 ml of dibutyltin dilaurate and 7.6 g of 3,5-dimethylphenyl isocyanate are added. The solution is stirred at 110° C. for 25 hours. After cooling to 60° C., 350 ml of methanol are added. The resulting suspension is filtered and the filter cake is washed with methanol. The crude product is dissolved in 200 ml of methylene chloride and the solution is filtered. The product is precipitated with 700 ml of methanol. The precipitate is filtered off and washed with methanol. Yield: 7.6 g. Elemental analysis: found: C 63.20; H 6.33; N 6.83; O 23.27.

Coating 0.63 g of that product is dissolved in 15 ml of tetrahydrofuran. The solution is divided into three portions. 2.5 g of aminosilanised silica (Nucleosil-4000, particle size 7 mm, Macherey-Nagel) are mixed with the three portions in succession, followed each time by concentration using a rotary evaporator. After drying in vacuo, 3.1 g of product are isolated.

Cross-linking 3 g of that material are suspended in 220 ml of hexane (isomeric mixture) and stirred. The suspension is irradiated with a submersible mercury lamp (Philips, HPK-125 Watt) for 16 hours. The suspension is filtered and the filter cake is washed with hexane and dried. Yield 2.9 g. That product is extracted with methylene chloride in a Soxhlet apparatus for 16 hours. The insoluble residue is suspended in approximately 30 ml of methylene chloride, and 300 ml of hexane are added (rate of addition: 1.2 ml/min). The product is filtered off and washed with hexane.

Column Packing 2.5 g of the resulting material are made into a slurry in 25 ml of hexane/2-propanol (90:10, % by volume) and packed into a steel column (25 cm×0.4 cm) at a pressure of 100 bar using the slurry method.

EXAMPLE 2

2.67 g of Intermediate 16 are dried in a round-bottomed flask for 3 hours at a bath temperature of 120° C. with nitrogen flushing. Then 40 ml of pyridine, 0.1 ml of dibutyltin dilaurate and 7.6 g of 3,5-dimethylphenyl isocyanate are added. The solution is stirred at 110° C. for 25 hours. After cooling to 60° C., 350 ml of methanol are added. The resulting precipitate is filtered off and washed with methanol. The product is twice purified by dissolution in 150 ml of methylene chloride and precipitation with 600 ml of methanol. The precipitate is each time filtered off and washed with methanol. Yield: 7.4 g (product 21). Elemental analysis: Found: C 63.85; H 6.27; N 6.98; O 22.63.

Coating 0.63 g of that product is dissolved in 15 ml of tetrahydrofuran. The solution is divided into three portions. 2.5 g of aminosilanised silica (Nucleosil-4000, particle size 7 mm, Macherey-Nagel) are mixed with the three portions in succession, followed each time by concentration using a rotary evaporator. After drying in vacuo, 3.1 g of product are isolated.

Cross-linking 3 g of that material are suspended in 220 ml of hexane (isomeric mixture) and stirred. The suspension is irradiated with a submersible mercury lamp (Philips, HPK-125 Watt) for 16 hours. The precipitate is filtered off, washed with hexane and dried. Yield 2.9 g.

That product is extracted with methylene chloride in a Soxhlet apparatus for 16 hours. The insoluble residue is suspended in approximately 30 ml of methylene chloride, and 300 ml of hexane are added (rate of addition: 1.2 ml/min). The product is filtered off and washed with hexane.

Column Packing 2.5 g of the resulting material are made into a slurry in 25 ml of hexane/2-propanol (90:10, % by volume) and packed into a steel column (25 cm×0.4 cm) at a pressure of 100 bar using the slurry method.

EXAMPLE 3

Analogously to Example 2, 2.6 g of Intermediate 17 are reacted with 7.4 g of 3,5-dimethylphenyl isocyanate in 35 ml of pyridine and purified. Yield: 7.4 g. Elemental analysis: Found: C 63.94; H 6.31; N 6.90; O 22.51. The coating is carried out analogously using 1.04 g of that product and 4 g of aminosilanised silica with 24 ml of tetrahydrofuran (3 portions). Yield: 5 g. Cross-linking of 3 g of that material yields 2.9 g of the chiral stationary phase, which is extracted with methylene chloride and washed with hexane (analogously to Example 2). The column packing is carried out in accordance with Example 2.

EXAMPLE 4

Analogously to Example 2, 1.85 g of Intermediate 18 are reacted with 5.9 g of 3,5-dimethylphenyl isocyanate in 30 ml of pyridine and purified. Yield: 5 g. Elemental analysis: Found: C 64.26; H 6.29; N 7.09; O 22.26. The coating is likewise carried out analogously using 0.63 g of that product and 2.5 g of aminosilanised silica with 15 ml of tetrahydrofuran (3 portions). Yield: 3.1 g. Cross-linking of 3 g of that material yields 2.9 g of the chiral stationary phase, which is extracted with methylene chloride and washed with hexane (analogously to Example 2). The column packing is carried out in accordance with Example 2.

EXAMPLE 5

Analogously to Example 2, 1.9 g of Intermediate 19 are reacted with 5.9 g of 3,5-dimethylphenyl isocyanate in 30 ml of pyridine and purified. Yield: 5 g. Elemental analysis: Found: C 63.50; H 6.27; N 7.14; O 22.91. The coating is likewise carried out analogously using 0.63 g of that product and 2.5 g of aminosilanised silica with 15 ml of tetrahydrofuran (3 portions). Yield: 3.1 g. Cross-linking of 3 g of that material yields 3 g of the chiral stationary phase, which is extracted with methylene chloride and washed with hexane (analogously to Example 2). The column packing is carried out in accordance with Example 2.

EXAMPLE 6

Analogously to Example 2, 2.6 g of Intermediate 12 are reacted with 7.6 g of 3,5-dimethylphenyl isocyanate in 40 ml of pyridine and purified. Yield: 6.9 g. Elemental analysis: Found: C 63.07; H 6.46; N 6.79; O 23.30. The coating is likewise carried out analogously using 0.63 g of that product and 2.5 g of aminosilanised silica with 15 ml of tetrahydrofuran (3 portions). Yield: 3.1 g. Cross-linking of 3 g of that material yields 3 g of the chiral stationary phase, which is extracted with methylene chloride and washed with hexane (analogously to Example 2). The column packing is carried out in accordance with Example 2.

EXAMPLE 7

Analogously to Example 2, 1.9 g of Intermediate 14 are reacted with 5.9 g of 3,5-dimethylphenyl isocyanate in 30 ml of pyridine and purified. Yield: 5.4 g. Elemental analysis: Found: C 64.02; H 6.23; N 6.63; O 23.11. The coating is likewise carried out analogously using 0.64 g of that product and 2.5 g of aminosilanised silica with 15 ml of tetrahydrofuran (3 portions). Yield: 3.1 g. Cross-linking of 3.0 g of that material yields 3.0 g of the chiral stationary phase, which is extracted with methylene chloride and washed with hexane (analogously to Example 2). The column packing is carried out in accordance with Example 2.

EXAMPLE 8

Analogously to the preparation of the product of Example 2, 1.8 g of Intermediate 20 are reacted with 5.9 g of 3,5-dimethylphenyl isocyanate in 30 ml of pyridine and purified. Yield: 5.0 g (product 22). Elemental analysis: Found: C 63.96; H 6.15; N 6.86; O 23.07. The coating is likewise carried out analogously using 1 g of that product and 4.0 g of aminosilanised silica with 24 ml of tetrahydrofuran (3 portions). Yield: 4.8 g. Cross-linking of 4.5 g of that material yields 4.3 g of the chiral stationary phase, which is extracted with methylene chloride and washed with hexane (analogously to Example 2). The column packing is carried out in accordance with Example 2.

EXAMPLE 9

4.0 g of product 21 from Example 2 are moistened with 15 ml of methanol. A solution of 12.8 g of N-phenyl-1-heptylcarbamate in 105 ml of methylene chloride is added. That solution is stirred until the cellulose derivative is completely dissolved and then 96 ml of a 5% polyvinyl alcohol solution (Serva, molecular weight approx. 90 000) are added dropwise to that solution in the course of 2.5 hours at room temperature and with vigorous stirring (500 rpm). The solution is then slowly heated to 42° C. and the methylene chloride is distilled off (about 2 hours). After cooling, the residue is filtered off, washed in portions with 500 ml of water and finally washed, in addition, with 200 ml of methanol. The resulting product is twice in succession suspended in 200 ml of methanol, stirred and filtered off. The product is then dried at room temperature. Yield: 3.7 g. The material consists of rounded particles having a particle size of from 20 to 30 µm. Specific surface according to BET: 2.6 m$^2$/g.

Cross-linking 5.2 g of that material are suspended in 300 ml of hexane (isomeric mixture) and stirred at 350 rpm. The suspension is irradiated with a submersible mercury lamp (Philips, HPK-125 Watt) for 16 hours. The precipitate is filtered off, washed with hexane and dried. Yield 5.2 g.

3.9 g of that product are extracted with methylene chloride in a Soxhlet apparatus for 17 hours. The insoluble residue is suspended in approximately 40 ml of methylene chloride, and 200 ml of hexane are added (rate of addition: 1 ml/min). The product is filtered off and washed in succession with 100 ml of hexane, with 400 ml of water, with 50 ml of ethanol and with 200 ml of hexane. Yield: 3.5 g.

Column Packing 2.5 g of the resulting material are made into a slurry in 25 ml of a mixture of hexane/2-propanol (85:15, % by volume) and packed using the slurry method into a steel column (25 cm×0.4 cm) at a flow rate of 2 ml/min over a period of 3 hours.

EXAMPLE 10

Analogously to Example 9, 10 g of product 22 (Example 8) are moistened with 38 ml of methanol, and a solution of 32 g of N-phenyl-1-heptylcarbamate in 262 ml of methylene chloride is added. After the methylene chloride has been distilled off and the solid residue worked up, 9.5 g of product are isolated. Yield: 95%. The material consists of rounded particles having particle sizes of from 20 to 30 µm. Specific surface according to BET: 2.1 m$^2$/g.

Cross-linking

Analogously to Example 9, 3.5 g of the isolated material are suspended in 250 ml of hexane and irradiated with a mercury lamp for 24 hours. After working-up, 3.4 g of the cross-linked material are isolated. Analogously to Example 9, that product is suspended in approximately 30 ml of methylene chloride, treated with 300 ml of hexane and washed. Yield: 3.2 g.

Column packing 2.5 g of the resulting material are made into a slurry in 25 ml of a mixture of hexane/2-propanol (90:10, % by volume) and packed using the slurry method into a steel column (25 cm×0.4 cm) at a flow rate of 2 ml/min over a period of 3 hours.

EXAMPLE 11

Analogously to Example 2, 1.8 g of Intermediate 16 are reacted with 4.8 g of phenyl isocyanate in 30 ml of pyridine and purified. Yield: 3.5 g. Elemental analysis: Found: C 59.46; H 5.09; N 7.73; O 27.42. The coating is likewise carried out analogously using 0.64 g of that product and 2.5 g of aminosilanised silica with 15 ml of tetrahydrofuran (3 portions). Yield: 3.1 g. Cross-linking of 3.0 g of that material yields 3.0 g of the chiral stationary phase, which is extracted with methylene chloride and washed with hexane (analogously to Example 2). The column packing is carried out in accordance with Example 2.

EXAMPLE 12

Analogously to Example 2, 1.8 g of Intermediate 16 are reacted with 5.3 g of phenyl isocyanate in 30 ml of pyridine and purified. Yield: 4.0 g. Elemental analysis: Found: C 60.99; H 5.77; N 7.36; O 25.23. The coating is likewise carried out analogously using 0.64 g of that product and 2.5 g of aminosilanised silica with 15 ml of tetrahydrofuran (3 portions). Yield: 3.1 g. Cross-linking of 3.0 g of that material yields 3.0 g of the chiral stationary phase, which is extracted with methylene chloride and washed with hexane (analogously to Example 2). The column packing is carried out in accordance with Example 2.

EXAMPLE 13

Analogously to Example 2, 1.7 g of Intermediate 12 are reacted with 5.3 g of 4-methylphenyl isocyanate in 30 ml of pyridine and purified. Yield: 4.2 g. Elemental analysis: Found: C 61.42; H 5.77; N 7.10; O 22.17. The coating is likewise carried out analogously using 0.64 g of that product and 2.5 g of aminosilanised silica with 15 ml of tetrahydrofuran (3 portions). Yield: 3.1 g. Cross-linking of 3.0 g of that material yields 3.0 g of the chiral stationary phase, which is extracted with methylene chloride and washed with hexane (analogously to Example 2). The column packing is carried out in accordance with Example 2.

EXAMPLE 14

Analogously to Example 2, 1.8 g of Intermediate 20 are reacted with 5.3 g of 4-methylphenyl isocyanate in 30 ml of pyridine and purified. Yield: 5.0 g. The coating is likewise carried out analogously using 0.65 g of that product and 2.5 g of aminosilanised silica with 15 ml of tetrahydrofuran (3 portions). Yield: 3.1 g. Elemental analysis: Found: C 61.21; H 5.74; N 7.28; O 25.40. Cross-linking of 3.0 g of that material yields 3.0 g of the chiral stationary phase, which is extracted with methylene chloride and washed with hexane (analogously to Example 2). The column packing is carried out in accordance with Example 2.

EXAMPLE 15

Analogously to Example 2, 1.67 g of Intermediate 16 are reacted with 5.3 g of 3,5-dimethylphenyl isocyanate in 30 ml of pyridine and purified. Yield: 5 g. Elemental analysis: Found: C 63.35; H 6.13; N 6.72; O 23.45. The coating is likewise carried out analogously using 0.63 g of that product and 2.5 g of aminosilanised silica with 15 ml of tetrahydrofuran (3 portions). Yield: 3.1 g. Cross-linking of 3 g of that material yields 3 g of the chiral stationary phase, which is extracted with methylene chloride and washed with hexane (analogously to Example 2). The column packing is carried out in accordance with Example 2.

EXAMPLE 16

Analogously to Example 2, 1 g of Intermediate 20 are reacted with 3.5 g of 3,4-dimethylphenyl isocyanate in 30 ml of pyridine and purified. Yield: 3.0 g. The coating is likewise carried out analogously using 0.64 g of that product and 2.5 g of aminosilanised silica with 15 ml of tetrahydrofuran (3 portions). Yield: 3.0 g. Cross-linking of 3.0 g of that material yields 3.0 g of the chiral stationary phase, which is extracted with methylene chloride and washed with hexane (analogously to Example 2). The column packing is carried out in accordance with Example 2.

EXAMPLE 17

Analogously to Example 2, 1.5 g of Intermediate 16 are reacted with 6.1 g of 4-chlorophenyl isocyanate in 30 ml of pyridine and purified. Yield: 4.4 g. Elemental analysis: Found: C 50.85; H 3.71; N 6.94; O 21.70; Cl 16.95. The coating is likewise carried out analogously using 0.64 g of that product and 2.5 g of aminosilanised silica with 15 ml of tetrahydrofuran (3 portions). Yield: 3.1 g. Cross-linking of 3 g of that material yields 3 g of the chiral stationary phase, which is extracted with methylene chloride and washed with hexane (analogously to Example 2). The column packing is carried out in accordance with Example 2.

EXAMPLE 18

1 g of Intermediate 13 is suspended in a mixture of 40 ml of pyridine and 12 ml of triethylamine in the presence of 10 mg of 4-dimethylaminopyridine. 7.5 ml of 4-methylbenzoic acid chloride are added to that suspension and the mixture is stirred under nitrogen at 90° C. for 23 hours. After cooling, the solution is poured into 200 ml of methanol and the precipitate is filtered off. The filter residue is twice in succession dissolved in methylene chloride, filtered off and precipitated in methanol. After drying in vacuo, 1.9 g of product are isolated.

Coating 3.0 g of aminosilanised silica (Nucleosil-4000, particle size 7 mm, Macherey-Nagel) are suspended in a solution of 1.0 g of that product in 67 ml of methylene chloride. 400 ml of hexane are added to the suspension, with stirring, at a rate of addition of 1 ml/min. The suspension is filtered and dried in vacuo. Yield: 3.9 g.

Cross-linking 3.5 g of that material are suspended in 300 ml of water/methanol (3:1, % by volume) and stirred at 400 rpm. The suspension is irradiated with a submersible mercury lamp (Philips, HPK-125 Watt) for 20 hours. The precipitate is filtered off, washed with hexane and dried. Yield 3.5 g.

That product is extracted with methylene chloride in a Soxhiet apparatus for 16 hours. The insoluble residue is suspended in approximately 30 ml of methylene chloride, and 180 ml of hexane are added at a rate of 1 ml/min. The product is filtered off and washed with hexane.

Column Packing 3.2 g of the resulting material are made into a slurry in 25 ml of hexane/2-propanol (90:10, % by volume) and packed using the slurry method into a steel column (25 cm×0.4 cm) at a flow rate of 2 ml/min over a period of 3 hours.

EXAMPLE 19

2.7 g of Intermediate 15 are suspended in a mixture of 86 ml of pyridine and 22 ml of triethylamine in the presence of 10 mg of 4-dimethylaminopyridine. 20 ml of 4-methylbenzoic acid chloride are added to that suspension and the mixture is stirred under nitrogen at 60° C. for 42 hours. After cooling, the solution is poured into 200 ml of methanol and the precipitate is filtered off. The filter residue is twice in succession dissolved in methylene chloride, filtered and precipitated in methanol. After drying in vacuo, 4.6 g of the product are isolated. The infrared spectrum no longer shows free hydroxy groups. The coating, cross-linking, extraction and column packing are carried out analogously to Example 18.

Testing of the Chiral Stationary Phases

The phases from Examples 1–17 are tested with the racemic structures 1–10 and with various mobile phases (Table 1). The phases from Examples 18 and 19 are tested with the racemic structures 2–5 and 11–15 and with various mobile phases (Table 2).

HPL chromatography is carried out using a Shimadzu LC-6A system with a flow rate of 0.7 ml/min and at room temperature. Detection is carried out by means of UV spectro-scopy and polarimetry (Perkin Elmer 241 LC). The separating factor a is determined as the measurement value.

$\alpha = k'_2/k'_1 = (t_2-t_0)/(t_1-t_0)$ where $k'_2$ and $k'_1$ are the capacity factors of the enantiomers eluted second and first, respectively, and $t_2$ and $t_1$ are the retention times thereof. $t_0$ is the elution time for tri-tert-butylbenzene (non-retained compound).

TABLE 1

| | $R_1$ | Racemate | | | | | | | | | | Mobile phase |
|---|---|---|---|---|---|---|---|---|---|---|---|---|
| | | 1 | 2 | 3 | 4 | 5 | 6 | 7 | 8 | 9 | 10 | |
| Example 1 | 3,5-dimethylphenyl-NHC(O)Me | 2.47 | 1.45 | 1.72 | 1.32 | 1.63 | 1.2 | | | | | hexane/2-propanol 9:1 |
| | | 2.53 | 1.49 | 1.47 | 1.44 | 1.43 | 1.47 | | | | | CH$_2$Cl$_2$/hexane/2-propanol 20:80:2.5 |
| | | 2.51 | 1.44 | 1.22 | 1.52 | 1.32 | 1.4 | | | | | CH$_2$Cl$_2$/hexane/2-propanol 40:60:2.5 |
| Example 3 | | 2.56 | 1.41 | 1.93 | 1.28 | 1.56 | | | | | | hexane/2-propanol 9:1 |
| | | 2.47 | 1.46 | 1.54 | | 1.43 | | | | | | CH$_2$Cl$_2$/hexane/2-propanol 20:80:2.5 |
| Example 2 | | 2.43 | 1.36 | 1.65 | 1.34 | 1.53 | | | | | | hexane/2-propanol 9:1 |
| Example 4 | | 2.25 | 1.47 | 1.75 | 1.38 | 1.64 | | | | | | hexane/2-propanol 9:1 |
| Example 5 | | 2.45 | 1.44 | 1.74 | 1.36 | 1.58 | | | | | | hexane/2-propanol 9:1 |
| Example 6 | | 2.74 | 1.47 | 1.9 | 1.32 | 1.66 | | | | | | hexane/2-propanol 9:1 |
| Example 7 | | 2.38 | 1.37 | 1.64 | 1.34 | 1.53 | | | | | | hexane/2-propanol 9:1 |
| Example 8 | | 2.64 | 1.45 | 1.79 | 1.36 | 1.65 | 1.17 | | 1.47 | 2.74 | 2.56 | hexane/2-propanol 9:1 |
| | | 2.63 | 1.49 | 1.53 | 1.5 | 1.49 | 1.58 | | 1.97 | 3.66 | 2.69 | CH$_2$Cl$_2$/hexane/2-propanol 20:80:2.5 |
| | | 2.54 | 1.43 | 1.37 | 1.58 | 1.35 | 1.43 | | 1.67 | 4.12 | 2.16 | CH$_2$Cl$_2$/hexane/2-propanol 40:60:2.5 |
| Example 9 | | 2.8 | 1.52 | 2 | 1.36 | 1.69 | | 1.58 | | 3.1 | | hexane/2-propanol 9:1 |
| Example 10 | | 2.79 | 1.52 | 1.88 | 1.34 | 1.73 | | 1.65 | | 3.14 | | hexane/2-propanol 9:1 |
| Example 11 | phenyl-NHC(O)Me | 1.41 | 1.08 | 1.31 | 1.29 | 1.23 | | 1.43 | 1.14 | 1.81 | | hexane/2-propanol 9:1 |
| | | 1.42 | 1 | 1.31 | 1.36 | 1.2 | | 1.63 | 1.28 | 1.99 | | CH$_2$Cl$_2$/hexane/2-propanol 20:80:2.5 |
| Example 12 | 4-methylphenyl-NHC(O)Me | 1.48 | 1 | 1.34 | 1.38 | 1.23 | | 1.21 | 1.32 | 2.16 | | hexane/2-propanol 9:1 |
| | | 1.53 | 1 | 1.37 | 1.48 | 1.23 | | 1.35 | 1.54 | 2.45 | | CH$_2$Cl$_2$/hexane/2-propanol 20:80:2.5 |
| Example 13 | | 1.66 | 1 | 1.53 | 1.41 | 1.32 | | | | | | hexane/2-propanol 9:1 |
| Example 14 | | 1.46 | 1 | 1 | 1.43 | 1.2 | | | 1.37 | 2.21 | | hexane/2-propanol 9:1 |
| Example 15 | 3,4-dimethylphenyl-NHC(O)Me | 1.84 | 1.24 | 1 | 1.63 | 1.65 | | | | | | hexane/2-propanol 9:1 |
| Example 16 | | 1.76 | 1.19 | 1.14 | 1.6 | 1.57 | | | | | | hexane/2-propanol 9:1 |
| Example 17 | 4-chlorophenyl-NHC(O)Me | 1.33 | 1 | 1.58 | 1.4 | 1.23 | | 1.21 | 1 | 1.95 | | hexane/2-propanol 9:1 |
| | | 1.3 | 1.08 | 1.55 | 1.52 | 1.19 | | 1.38 | 1.14 | 1.94 | | CH$_2$Cl$_2$/hexane/2-propanol 20:80:2.5 |

TABLE 2

| | $R_1$ | Racemate | | | | | | | | | Mobile phase |
|---|---|---|---|---|---|---|---|---|---|---|---|
| | | 2 | 3 | 4 | 5 | 11 | 12 | 13 | 14 | 15 | |
| Example 18 | 4-methylphenyl-C(O)- | 1.28 | 1.37 | 2.05 | 1.57 | 1.28 | 1.71 | 6.02 | 1.3 | 1.37 | hexane/2-propanol 9:1 |
| Example 19 | | 1.28 | 1.37 | 2.05 | 1.57 | 1.28 | 1.71 | 6.02 | 1.3 | 1.37 | hexane/2-propanol 9:1 |
| | | 1 | 1.21 | 1.93 | 1.64 | 2.04 | 1.31 | 2.4 | 1.18 | 1.11 | CH$_2$Cl$_2$/hexane/2-propanol 15:85:2.5 |

Racemic structures
1
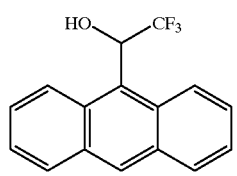
2
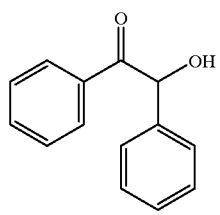
3
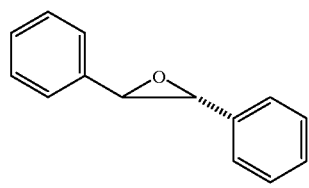
4
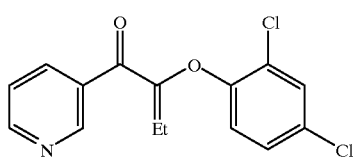
5
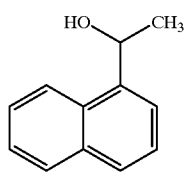
6
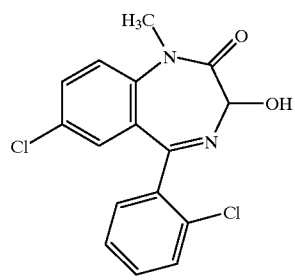
7
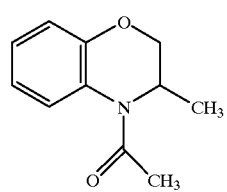
8
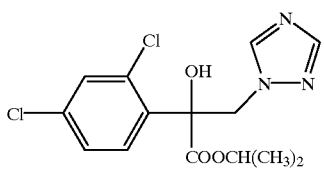
9
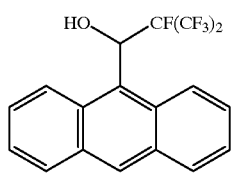
10
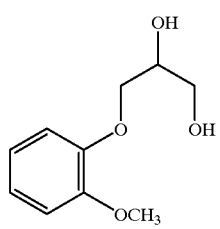
11
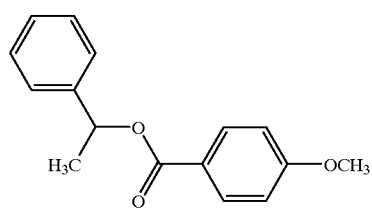
12
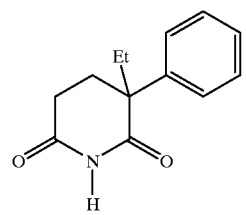
13
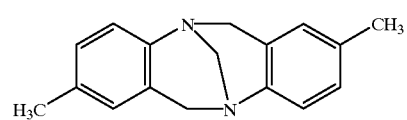
14
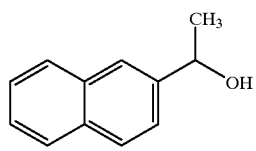
15
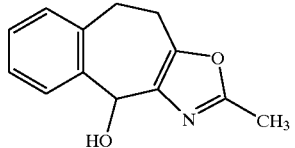
What is claimed is:
1. A photochemically cross-linked polysaccharide derivative of formula IA or IB

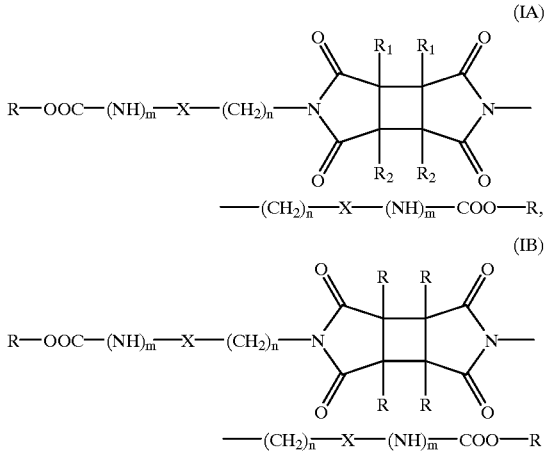

wherein
R is a cellulose or amylose radical having OH groups esterified to form —OCOAr or converted to form —OCONHAr;
Ar is a substituted or unsubstituted phenyl;
$R_1$ and $R_2$ are each independently lower alkyl or unsubstituted or substituted aryl;
X is a direct bond or phenylene;
m is 0 or 1; and
n is 0 or an integer from 1 to 20.

2. A polysaccharide derivative of claim 1 wherein
$R_1$ and $R_2$ are each independently methyl or ethyl or an unsubstituted or substituted phenyl; and
n is 0 or an integer from 1 to 12.

3. A polysaccharide derivative of claim 1 wherein
R is a cellulose radical;
$R_1$ and $R_2$ are each methyl; and
n is 0 or an integer from 1 to 12.

4. A polysaccharide compound of formula II

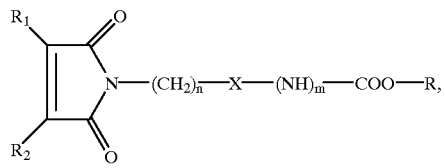

wherein
R is a cellulose or amylose radical having OH groups esterified to form —OCOAr or converted to form —OCONHAr;
Ar is a substituted or unsubstituted phenyl;
$R_1$ and $R_2$ are each independently lower alkyl or unsubstituted or substituted aryl;
X is a direct bond or phenylene;
m is 0 or 1; and
n is 0 or an integer from 1 to 20.

5. A polysaccharide compound of claim 4, wherein
$R_1$ and $R_2$ are each independently methyl or unsubstituted or substituted phenyl.

6. A polysaccharide compound of claim 4, wherein
$R_1$ and $R_2$ are each methyl.

7. A process for the preparation of a polysaccharide compound of claim 4, wherein a compound of formula III

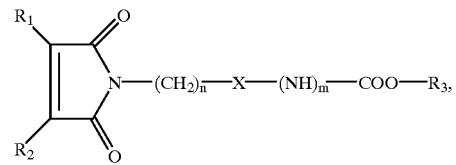

wherein
$R_3$ is a cellulose or amylose radical having free OH groups, is reacted to esterify or convert free OH groups to —OCOAr or to —OCONHAr, wherein Ar is substituted or unsubstituted phenyl.

8. A process of claim 7, wherein esterification of the compound of formula III is effected with a reactive functional carboxylic acid derivative.

9. A process of claim 7, wherein the conversion into a carbamate of a compound of formula III is effected by reaction with an isocyanate.

10. A process of claim 9 wherein the reaction with an isocyanate is carried out in the presence of a Lewis base or a Lewis acid as catalyst.

11. A polysaccharide compound of formula III

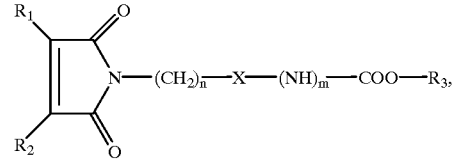

wherein
$R_3$ is a cellulose or amylose radical having free OH groups;
$R_1$ and $R_2$ are each independently lower alkyl or unsubstituted or substituted aryl;
X is a direct bond or phenylene;
m is 0 or 1; and
n is 0 or an integer from 1 to 20.

12. A polysaccharide compound of claim 11 wherein $R_1$ and $R_2$ are each independently methyl or unsubstituted or substituted phenyl.

13. A polysaccharide compound of claim 11 wherein $R_1$ and $R_2$ are each methyl.

14. A process for the preparation of a compound of claim 11 wherein cellulose or amylose having free OH groups is converted into a carbamate or esterified with an imidylcarboxylic acid halide or isocyanate of formula IV

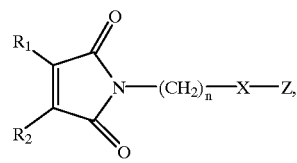

wherein
Z is an isocyanate (—N=C=O) group or a carboxylic acid halide group, optionally in the presence of a catalyst.

15. A process of claim 14, wherein the cellulose or amylose having free OH groups is reacted with an imidyl-carboxylic acid halide of formula IV in the presence of a basic condensation agent.

16. A process of claim 14, wherein the cellulose or amylose having free OH groups is reacted with an imidyl isocyanate of formula IV in the presence of dibutyltin dilaurate.

17. A process for the preparation of a polysaccharide derivative of claim 1, wherein the process comprises (1) applying a compound of formula II

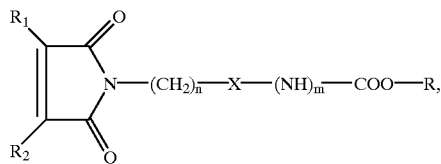

as a coating to a support, or after conditioning it, as a pure material emulsion; and then (2) cross-linking the compound of formula II by irradiation to form a compound of formula of IA or IB.

18. A process of claim 17 wherein the cross-linking is effected by irradiation using a submersible mercury lamp.

19. A process of claim 17 wherein the coating support is silica gel, aluminum oxide (alumina), graphite, or zirconium oxide.

20. A process of claim 17 wherein an inert solvent is used for the preparation of a suspension.

21. A photochemically cross-linked polysaccharide derivative of formula IA or IB obtainable by the process of claim 17.

* * * * *